US011868767B2

(12) United States Patent
Ukis et al.

(10) Patent No.: US 11,868,767 B2
(45) Date of Patent: Jan. 9, 2024

(54) COMPUTER-IMPLEMENTED RUNTIME SYSTEM, HEALTHCARE NETWORK, METHOD AND COMPUTER PROGRAM

(71) Applicant: Siemens Healthcare GmbH, Erlangen (DE)

(72) Inventors: Vladyslav Ukis, Nuremberg (DE); Lutz Dominick, Eggolsheim (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 287 days.

(21) Appl. No.: 17/330,608

(22) Filed: May 26, 2021

(65) Prior Publication Data
US 2021/0373884 A1 Dec. 2, 2021

(30) Foreign Application Priority Data
Jun. 2, 2020 (DE) ...................... 10 2020 206 861.5

(51) Int. Cl.
*G06F 11/20* (2006.01)
*G06F 11/30* (2006.01)
(Continued)

(52) U.S. Cl.
CPC .............. *G06F 8/77* (2013.01); *G06F 11/143* (2013.01); *G06F 11/1492* (2013.01);
(Continued)

(58) Field of Classification Search
CPC ...... G06F 8/77; G06F 11/143; G06F 11/1492; G06F 11/1469; G06F 11/008;
(Continued)

(56) References Cited

U.S. PATENT DOCUMENTS

| 2003/0095648 A1* | 5/2003 | Kaib | ................... A61B 5/0006 379/106.02 |
| 2004/0031030 A1* | 2/2004 | Kidder | ................... H04L 41/22 717/172 |

(Continued)

FOREIGN PATENT DOCUMENTS

| EP | 2381363 A2 | 10/2011 |
| EP | 3457408 A1 | 3/2019 |
| EP | 3567600 A1 | 11/2019 |

OTHER PUBLICATIONS

Wubin Li et al., Leveraging Linux Containers to Achieve High Availability for Cloud Services, 2015 IEEE, [Retrieved on Aug. 14, 2023]. Retrieved from the internet: <URL: https://ieeexplore.ieee.org/stamp/stamp.jsp?tp=&arnumber=7092902> 8 Pages (76-83) (Year: 2015).*

(Continued)

*Primary Examiner* — Anibal Rivera
(74) *Attorney, Agent, or Firm* — Harness, Dickey & Pierce, P.L.C.

(57) ABSTRACT

A computer-implemented runtime system is operable of providing a continuous product execution runtime environment for an application via a healthcare network. The system includes a focus machine and an action plan repository, to provide an autonomous runtime environment by at least: monitoring a running use case of at least one application on at least one device; taking over responsibility of a running use case of the at least one application, upon an error state being detected for the monitored running use case; analyzing the error state of the running use case detected; obtaining at least one suitable substitution action out of a plurality of actions deposited in the action plan repository, based on the error state of the running use case analyzed; and terminating and completing at least a part of the running use case, by (Continued)

employing the at least one substitution actions obtained, on the at least one application.

21 Claims, 3 Drawing Sheets

(51) Int. Cl.

| | | |
|---|---|---|
| *G06F 11/34* | (2006.01) | |
| *G06F 9/44* | (2018.01) | |
| *G06F 11/36* | (2006.01) | |
| *G06F 8/77* | (2018.01) | |
| *G16H 40/60* | (2018.01) | |
| *G06F 11/14* | (2006.01) | |
| *H04L 41/0663* | (2022.01) | |
| *H04L 41/0859* | (2022.01) | |
| *G06F 11/07* | (2006.01) | |
| *H04L 41/0654* | (2022.01) | |
| *G06F 11/00* | (2006.01) | |

(52) U.S. Cl.
CPC ........... *G16H 40/60* (2018.01); *G06F 11/008* (2013.01); *G06F 11/079* (2013.01); *G06F 11/0793* (2013.01); *G06F 11/1458* (2013.01); *G06F 11/1469* (2013.01); *H04L 41/0654* (2013.01); *H04L 41/0663* (2013.01); *H04L 41/0863* (2013.01)

(58) Field of Classification Search
CPC ............... G06F 11/079; G06F 11/0793; G06F 11/1458; G16H 40/60; G16H 40/40; H04L 41/0654; H04L 41/0663; H04L 41/0863

See application file for complete search history.

(56) References Cited

U.S. PATENT DOCUMENTS

| | | | |
|---|---|---|---|
| 2008/0235659 A1* | 9/2008 | Manglik | G06F 11/366 717/111 |
| 2009/0119067 A1* | 5/2009 | Stempfer | A61B 6/56 702/184 |
| 2011/0265164 A1 | 10/2011 | Lucovsky et al. | |
| 2013/0339958 A1 | 12/2013 | Droste et al. | |
| 2014/0201565 A1* | 7/2014 | Candea | G06F 11/2069 714/15 |
| 2017/0102997 A1* | 4/2017 | Purushothaman | G06F 11/079 |
| 2018/0285204 A1* | 10/2018 | Dwarampudi | G06F 11/302 |
| 2019/0088358 A1 | 3/2019 | Dominick et al. | |
| 2019/0347186 A1 | 11/2019 | Dominick et al. | |
| 2020/0349133 A1* | 11/2020 | Dwarampudi | G06F 16/219 |
| 2021/0286689 A1* | 9/2021 | Dehganpour | G06F 11/2028 |

OTHER PUBLICATIONS

German Office Action dated Jan. 20, 2021.

* cited by examiner

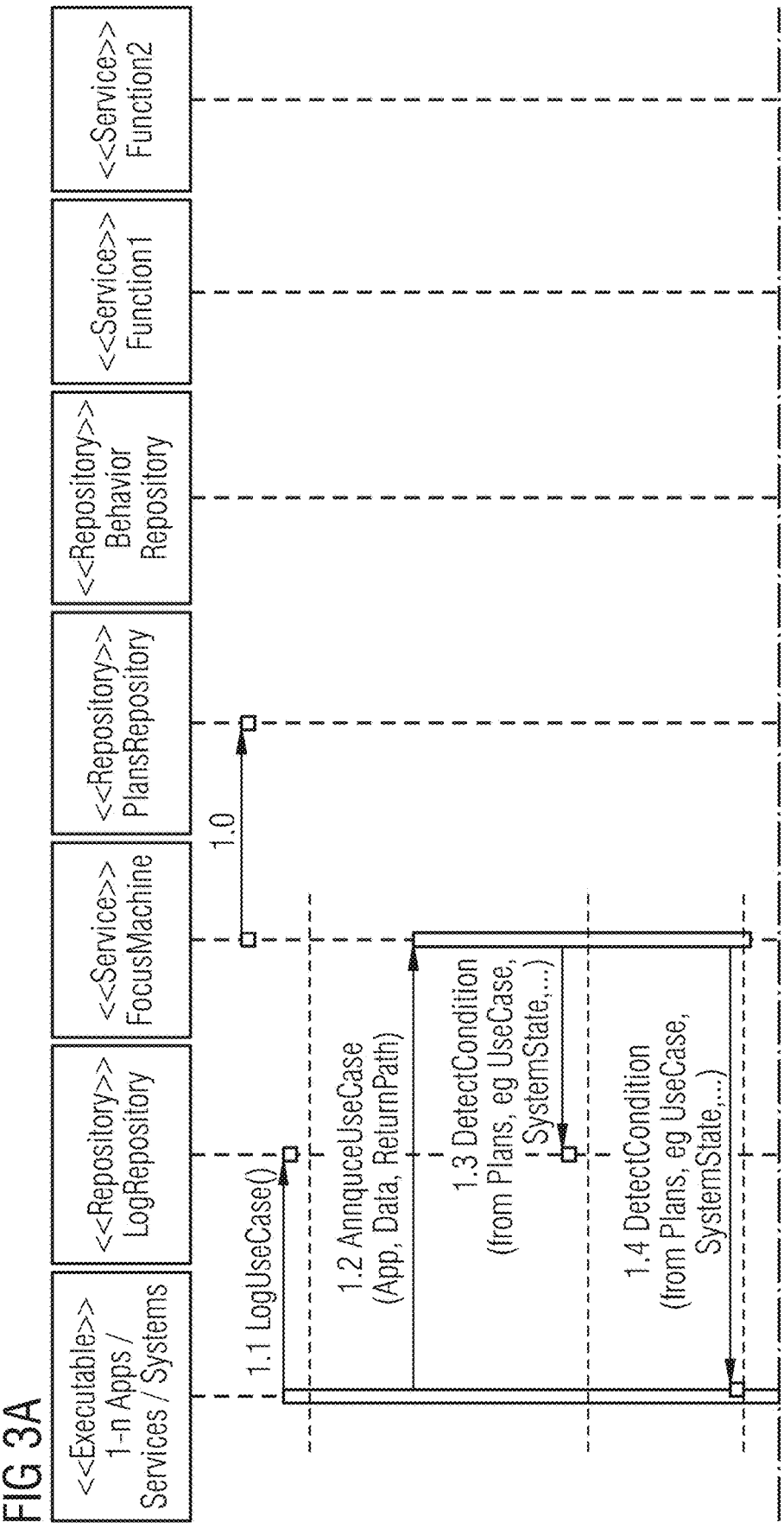

COMPUTER-IMPLEMENTED RUNTIME SYSTEM, HEALTHCARE NETWORK, METHOD AND COMPUTER PROGRAM

PRIORITY STATEMENT

The present application hereby claims priority under 35 U.S.C. § 119 to German patent application number DE 102020206861.5 filed Jun. 2, 2020, the entire contents of which are hereby incorporated herein by reference.

FIELD

Example embodiments of the invention generally relate to a computer-implemented runtime system; a healthcare network; a method and to a computer program.

BACKGROUND

The example embodiments of present invention are generally in the area of healthcare networks, e.g. such as described in EP 3 457 408 A1 and EP 3 567 600 A1.

A healthcare network comprises a plurality of systems including devices, products, platforms and applications (also referred to as software, programs or computer programs). The devices may include medical devices (e.g. a picture archiving and communication system (PACS), an ultrasound system, etc.), user terminals for use by medical professionals and patients, specialist user terminals (e.g. nurse call system), servers and medical data stores. The platforms facilitate the devices and applications to access services and repositories internal or external to the healthcare network. Applications operate on, or in conjunction with or accessible via the devices, and may include communication applications that facilitate communication between the devices on the healthcare network, medical applications configured to process medical information, applications configured to manage patent information, applications for managing knowledge in a healthcare environment, applications configured to manage medical records.

Such modern medical application environments are complex and use a variety of different devices and products, from different manufacturers, in a heterogeneous landscape and infrastructure with heterogeneous functions and applications and often in a non-standardized manner. In particular, the trend in the architecture of modern medical devices and products goes towards a growing number of comparably small systems, applications and services that are interconnected and interacting with each other instead of using only a few comparably complex system or isolated products.

In such a heterogeneous landscape architecture having an increasing number of comparably independently operated systems, applications and services, the probability for unwanted situations and system errors increases, both for the different products and devices and for the interaction between them. If, for example, a situation at operation times is beyond a so-called happy path, the application can no more handle the corresponding use case. As a consequence of this, the application gets stuck.

Users who seek for a quick way out of this situation, are according to a typical approach often confronted with an error dialog, or even worse, with an exception dialog and leaves him with a phone number of the service help desk. Besides the fact, that these remote service help desks are often not available if they are needed, they are often not productive, so that the user often cannot escape from this error situation. This mostly leads to the need to restart an ongoing use case without the guarantee that the same error situation occurs again. Often the work and the data of the interrupted use case are no more recoverable.

SUMMARY

For background activity, watch dog mechanisms are known that provide low level actions like start, restarts or reboots, which however neither deal with error prevention or correction nor with a suitable use case continuation.

Against this background, a problem addressed by at least one embodiment of the present invention is to improve the handling of ongoing use cases of application that are stuck.

Embodiments are directed to a computer-implemented runtime system and/or a healthcare network and/or a method and/or a computer program.

According thereto, at least one embodiment is directed to a computer-implemented runtime system operable of providing a continuous product execution runtime environment for at least one application via a healthcare network, the healthcare network comprising a plurality of production devices configured to process medical information of the runtime environment, wherein the runtime system further comprises a focus machine and an action plan repository which are configured to provide an autonomous runtime environment by: Monitoring a running use case of an application on at least one device by the focus machine; Taking over the responsibility of the running use case of the application by the focus machine in case an error state is detected for the monitored running use case; Analyzing the detected error state of the running use case by the focus machine; Obtaining at least one suitable substitution action out of a plurality of actions deposited in the action plan repository based on the analyzed error state of the running use case; and Terminating and preferably completing the running use case or parts of it by the focus machine by employing the obtained substitution actions on the application.

At least one embodiment is further directed to a healthcare network, comprising: a plurality of production devices operable by a plurality of users and configured to process medical information, and at least one runtime system according to an embodiment of the present invention, the runtime system having at least one interface for coupling to the plurality of production devices and configured to provide an autonomous runtime environment for the plurality of production devices.

At least one embodiment is further directed to a computer-implemented runtime method of providing a continuous and autonomous product execution runtime environment for at least one application, comprising: Providing a healthcare network comprising a plurality of production devices configured to process medical information of the runtime environment; Monitoring a running use case of an application on at least one device via an interface of the healthcare network; Taking over the responsibility of the running use case of the application by an externally provided focus machine in case an error state is detected for the monitored running use case; Analyzing the detected error state of the running use case by the focus machine; Obtaining at least one suitable action out of a plurality of actions based on the analyzed error state of the running use case; and Terminating and preferably completing the running use case or parts of it by the focus machine by employing the obtained actions on the application.

At least one embodiment is further directed to a computer program, stored upon a non-transitory computer readable medium, comprising a set of instructions which, when executed by a computerized device, cause the computerized electronic device to perform a method according to an embodiment of the present invention.

At least one embodiment is further directed to a computer-implemented runtime system operable to provide a continuous product execution runtime environment for at least one application via a healthcare network, the healthcare network including a plurality of production devices configured to process medical information of the runtime environment, the computer-implemented runtime system comprising:
- a focus machine and an action plan repository, configured to provide an autonomous runtime environment by at least:
  - monitoring a running use case of at least one application on at least one device via the focus machine;
  - taking over responsibility of a running use case of the at least one application via the focus machine, upon an error state being detected for the monitored running use case;
  - analyzing the error state of the running use case detected, via the focus machine;
  - obtaining at least one suitable substitution action out of a plurality of actions deposited in the action plan repository, based on the error state of the running use case analyzed; and
  - terminating and completing at least a part of the running use case via the focus machine, by employing the at least one substitution actions obtained, on the at least one application.

At least one embodiment is further directed to a healthcare network, comprising:
- a plurality of production devices, operable by a plurality of users and configured to process medical information; and
- at least one computer-implemented runtime system of an embodiment, the at least one computer-implemented runtime system including at least one interface for coupling to the plurality of production devices and configured to provide an autonomous runtime environment for the plurality of production devices.

At least one embodiment is further directed to a computer-implemented runtime method of providing a continuous and autonomous product execution runtime environment for at least one application, comprising:
- providing a healthcare network including a plurality of production devices, configured to process medical information of the runtime environment;
- monitoring a running use case of an application on at least one production device, of the plurality of production devices, via an interface of the healthcare network;
- taking over responsibility of the running use case of the at least one application via an externally provided focus machine, upon an error state being detected for the running use case monitored;
- analyzing the error state of the running use case detected, via the focus machine;
- obtaining at least one suitable action out of a plurality of actions, based on the error state of the running use case analyzed; and
- terminating and completing at least a part of the running use case via the focus machine, by employing the obtained actions on the at least one application.

At least one embodiment is further directed to a non-transitory computer program product storing a set of instructions which, when executed by a computerized device, cause the computerized electronic device to perform the computer-implemented runtime method of an embodiment.

At least one embodiment is further directed to a non-transitory computer readable storing a set of instructions which, when executed by a computerized device, cause the computerized electronic device to perform the computer-implemented runtime method of an embodiment.

BRIEF DESCRIPTION OF THE DRAWINGS

The present invention is described in greater detail in the following on the basis of the embodiments shown in the schematic figures of the drawings, in which.

Figure 1:
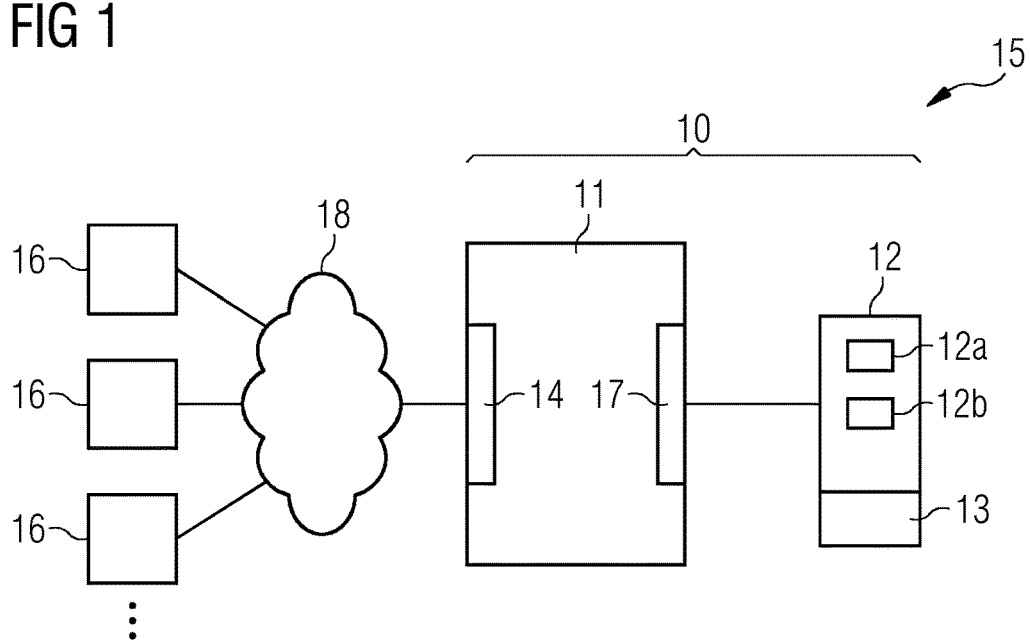
FIG. 1 shows a block diagram illustrating a computer-implemented runtime system within a healthcare network operable according to an embodiment of the present invention.

The appended drawings are intended to provide further understanding of the embodiments of the invention. They illustrate embodiments and, in conjunction with the description, help to explain principles and concepts of the invention. Other embodiments and many of the advantages mentioned become apparent in view of the drawings. The elements in the drawings are not necessarily shown to scale.

In the drawings, like, functionally equivalent and identically operating elements, features and components are provided with like reference signs in each case, unless stated otherwise.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According thereto, at least one embodiment is directed to a computer-implemented runtime system operable of providing a continuous product execution runtime environment for at least one application via a healthcare network, the healthcare network comprising a plurality of production devices configured to process medical information of the runtime environment, wherein the runtime system further comprises a focus machine and an action plan repository which are configured to provide an autonomous runtime environment by: Monitoring a running use case of an application on at least one device by the focus machine; Taking over the responsibility of the running use case of the application by the focus machine in case an error state is detected for the monitored running use case; Analyzing the detected error state of the running use case by the focus machine; Obtaining at least one suitable substitution action out of a plurality of actions deposited in the action plan repository based on the analyzed error state of the running use case; and Terminating and preferably completing the running use case or parts of it by the focus machine by employing the obtained substitution actions on the application.

At least one embodiment is further directed to a healthcare network, comprising: a plurality of production devices operable by a plurality of users and configured to process medical information, and at least one runtime system according to an embodiment of the present invention, the runtime system having at least one interface for coupling to the plurality of production devices and configured to provide an autonomous runtime environment for the plurality of production devices.

At least one embodiment is further directed to a computer-implemented runtime method of providing a continuous and autonomous product execution runtime environment for at least one application, comprising: Providing a healthcare network comprising a plurality of production devices configured to process medical information of the runtime environment; Monitoring a running use case of an application on at least one device via an interface of the healthcare network; Taking over the responsibility of the running use case of the application by an externally provided focus machine in case an error state is detected for the monitored running use case; Analyzing the detected error state of the running use case by the focus machine; Obtaining at least one suitable action out of a plurality of actions based on the analyzed error state of the running use case; and Terminating and preferably completing the running use case or parts of it by the focus machine by employing the obtained actions on the application.

According thereto, at least one embodiment is further directed to a computer program, stored upon a non-transitory computer readable medium, comprising a set of instructions which, when executed by a computerized device, cause the computerized electronic device to perform a method according to an embodiment of the present invention.

The focus of the approach according to at least one embodiment of the invention is that of providing an autonomous product execution environment that handles use cases, situations, incidents and the like in an automated and/or autonomous manner. In particular, use cases are handled by preserving operational data and use case context, with dedicated choices of applicable actions and decision autonomy.

The proposed solution according to at least one embodiment of the present invention provides an autonomous, preferably cloud based runtime environment that is configured to make suitable autonomous decisions on when, if, and how to proceed with an ongoing use case or situation at runtime. The autonomous runtime environment thereby can become active, already in situations that are not known in the running or installed systems, application and/or services.

The new autonomous runtime environment implies a shift and hand-over of the responsibility of an ongoing defective use case to an externally arranged focus machine. For a next step of this ongoing defective use case, the focus machine of the runtime system proceeds with the ongoing use case based on a number of configurable actions. At best, the focus machine is completing the defective use case instead of the original use case owner, such as the production device. This format of a use case that is executed externally allows the safe handling of unproductive dead-end-situations.

The application behavior seems to continue an interrupted use case automatically and autonomously, without further user interaction or additional information. For this purpose, the application notifies the need for substituting a current execution path of the defective use case with an alternative execution path for the current defective use case. This way, a faulty (or at least a non-typical) behavior of the app, software or program is masked-out by employing an appropriate, use case compatible functional substitution.

Known solutions, as the ones described in the introductory part, do neither structure nor distribute functionality in this novel approach. In known solutions, a use case execution is treated as an exclusive inside-responsibility of the corresponding application or service. The novel approach according to the present invention provides instead a technical focus machine to conditionally shift this responsibility for the faulty or defective use case (or use case step) to a different program outside the set of available programs. Neither the initial application or service nor the focus machine can know a priori what next program is due and which one of the next programs resolves the required next step in the use case successfully, which in turn completes the use case with or even without the initial application or service. One core aspect of the present invention is, thus, that the focus machine does not define, redefine or modify existing use cases, even if they produce error states.

This kind of autonomous runtime environment provides a most flexible alignment with running use cases by employing a substituting functionality. In particular, the autonomous runtime system tries to complete a known or unknown running use case, if, for example, this specific use case got stuck, or if a user of an application received an exception that neither the user nor the application itself can handle. Then, the autonomous runtime system helps to release the application from the exception, continues with the application and/or completes the use case successfully. Time-consuming interruptions are thereby avoided as far as possible. In addition, the prior work of the user is preserved and thus not lost.

The infrastructure of the autonomous runtime system is comprised of set of suitable interfaces and components that are configured to execute the working models, storyboards and/or action plans. According to the present invention, at least one application or service runs on a production device. The autonomous runtime environment includes a so-called focus machine that is configured to execute so-called action plans. These action plans contain conditions, action lists and the like which are necessary to proceed with a running use case. The autonomous runtime environment may also include auxiliary repositories such as plan repository which comprise downloadable action plans and behavior repository with configured and updated metrics from use case behavior aspects. Further, already at development or later in the process, an action plan generator collects the available action plans during the software development. These action plans are then transmitted and deployed with the software to a cloud based production environment, both during product shipment to cloud production and as add-on on-the-fly at any time.

One main advantage of at least one embodiment of the present invention is that the substitution actions that substitute the faulty or stuck use case or use case steps are not part of the corresponding application or service. This ensures that the substitution actions are technically executable, whenever triggered, even if the corresponding application or service, respectively, were not able to do so, e.g. the internal control flow is not prepared for the situation.

Advantageous configurations and developments emerge from the further claims and from the description with reference to the figures of the drawings.

According to a preferred embodiment, the focus machine is further configured to provide the data of the completed use case or parts of it to the production device and/or the runtime environment. Preferably, this function of providing the data of the completed use case or parts of it includes: Storing by the focus machine the data of the completed use case or parts of it in the action plan repository.

According to an embodiment, the function of taking over responsibility includes: Detecting the error state of the monitored use case by the focus machine in the case that the detected state of a running use case fulfills at least one predefined condition. Here, the predefined condition of a running use may be a dead end situation of a use case where the execution of the corresponding application is stopped. Additionally or alternatively, the predefined condition of a running use case may also be a predefined deviation of the executed application from a happy path of the use case.

According to a further embodiment, the functions of taking over responsibility and analyzing the detected error state include: Generating by the focus machine a priority of conditions from a list of available conditions; and reading by the focus machine from the action plan repository suitable behavior metrics which correspond to the generated priority.

In a preferred configuration, the function of obtaining at least one suitable substitution action includes: Deciding by the focus machine which condition is to be applied in the present stage of the use case; and determining by the focus machine the actions and the order in which these actions are to be executed in the present stage of the use case.

According to a further embodiment, the function of terminating a running use case or parts of it includes an autonomous success control monitoring by the focus machine by monitoring the success of the executed actions and by storing the success information in the action plan repository.

According to a specifically preferred embodiment, the healthcare network is operable of providing a cloud-based runtime environment. In particular, the autonomous runtime environment is pluggable to the production in the cloud.

Where appropriate, the above-mentioned configurations and developments can be combined in any manner. Further possible configurations, developments and implementations of the invention also include combinations, which are not explicitly mentioned, of features of the invention which have been described previously or are described in the following with reference to the embodiments. In particular, in this case, a person skilled in the art will also add individual aspects as improvements or supplements to the basic form of the present invention.

FIG. 1 shows a block diagram illustrating a computer-implemented runtime system within a healthcare network operable according to the present invention.

The runtime system is configured to provide a continuous product execution runtime environment for at least one application via a healthcare network. The healthcare network, which may be a cloud-based online network such as Siemens Healthineers' "Teamplay", is configured to connect a plurality of production devices. These devices are configured to process medical information of the runtime environment, e.g. by executing software applications, services and/or other kinds of software products.

In FIG. 1, the runtime system is denoted by reference numeral 10. The runtime system 10 is part of a healthcare network 15.

The runtime system 10 comprises—amongst—others a focus machine 11, an action plan repository 12 and optionally an action plan generator 13. The focus machine 11 comprises a first interface 14 for coupling the runtime system 10 via an interface 18 of the healthcare network 15 to one or more production devices 16. The focus machine 11 further comprises a second interface 17 for coupling to the action plan repository 12. In the embodiment shown in FIG. 1, the action plan generator 13 is part of the action plan repository 12. Additionally or alternatively, the action plan generator 13 may also be part of the focus machine 11 or coupled to the focus machine 11 or action plan generator 13 via the healthcare network 15 (not shown in FIG. 1).

The production devices 16 are used to execute a specific application, service or system. An application, service or system—hereinafter simply referred to as app—in the context of the present invention denotes types of software programs that implement and provide the execution of use cases on purpose, that create internal and external conditions. These apps are exposed to conditions in the runtime context at the same time. Such use cases process dedicated data and are expected to produce dedicated and predefined results after a set of use case steps and after some processing time. This gives measurable behavior in space and time of multiple of such programs, which in turn can be traced and be matched to conditions in the action plans, and also further actions, that cannot be part of a single use case, for example.

The action plan repository 12 comprises a plurality of suitable action plans. In particular, the action plan repository 12 includes auxiliary repositories like downloadable action plans 12a and behavior repository 12b with configured and updated metrics from use case behavior aspects. An action plan in the context of the present invention consists of conditions and a list of suitable actions. Specifically, the action plan repository 12 combines a set of predefined conditions, that can be automatically monitored, measured and detected in a mixture of applications, services or systems, with a list of corresponding suitable actions, that could be performed if the predefined conditions are fulfilled. The objective for providing an action plan is to complete an ongoing use case that is stuck, caused an error, deviated from the happy path or the like. Alternatively, an action plan may also be needed to meet a situation with suitable actions because the conditions show that the original ongoing use case might not meet its post-conditions, or even got stuck. The suitable actions in the list of actions is the functional substitution of the original control flow (or happy path) that was defined to be used in a best case scenario during development. Preferably, a plurality of actions are provided, that are different to each other since it is not known a priori what action can render the successful result that is required for the use case or for the given situation. A suitable action plan can be created for all types and sizes of scope (i.e. all systems/products, a subset of the systems/products, or only one or a few applications/services). A suitable action plan can also be created for all conditions that can be detected in an automated and/or autonomous manner. Actions, therefore, can have an auxiliary, corrective, optimizing, etc. character.

The action plan generator 13 provides, preferably but not compulsory during development, the action plans. For example, during development the action plan generator 13 is used to compile the action plans that need to be combined with the software and that is to be deployed in the cloud based production environment. The set of action plans can depend e.g. on the version of the parts, applications and services of the overall software product, the types and number of cooperating systems and specifics of the target deployment, like intended and faulty runtime behavior and related conditions and actions in the action plans. The action plan generator 13 can take into consideration these characteristics.

The focus machine 11 which is the core component of the runtime system 10 denotes a control device that acts as a monitoring and control instance for guaranteeing that an ongoing use case is finished properly. The focus machine 11 may be a programmable control device, such as a computer, a microprocessor, a controller or the like. The focus machine 11 mainly executes the action plans provided by the action plan repository 12. For this purpose, the focus machine 11 monitors an ongoing use case of an app as input data and measures if a predefined error condition is met. If a predefined error condition is met, the focus machine 11 takes over the responsibility of this ongoing use case automatically and preferably also autonomously. In particular, the focus machine 11 fetches one or more substitution action plans provided by the action plan repository 12 as input data in order to execute the action list of the substitution action plans and in order to provide a substitution result for the ongoing use case. Especially important in this context is the fact that the substitution actions that are used by the focus machine 11 to substitute the functionality of the ongoing use case or parts of it are not part of the faulty app. This is in particular smart as this ensures that the substitution actions are technically executable at any time, when triggered, even if the app is no more able to do so e.g. due to the internal control flow is not prepared for this specific error situation.

Summarizing, the focus machine 11 comprises, amongst other functionalities, the following monitoring and control mechanism for an ongoing use case:
Executing technical impacts;
Monitoring alert information;
Analyzing log data;
Analyzing metric data;
Detecting anomalies in the data produced by the apps;
Distributing feedback information to the production device via the first interface;
Before/after deploy analysis (incl. spot test with domain model).

The focus machine 11 may also comprise the action plan repository 12 (not shown in FIG. 1).

Figure 2:
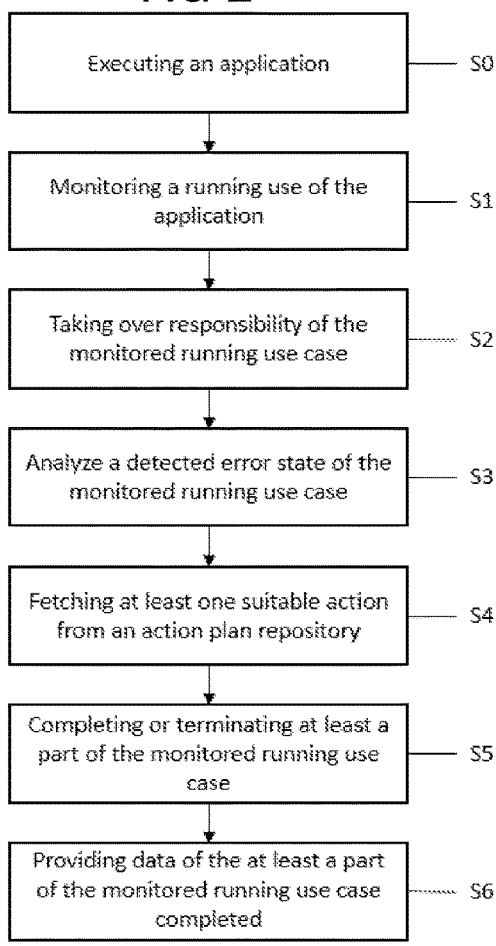
FIG. 2 shows a flowchart for illustrating the functionality of the runtime system.

In the following, the functionality of the runtime system 10 is briefly explained using the flowchart of FIG. 2:

The one or more production devices 16 of the healthcare network 15 are executing one or more apps (step S0). In a normal operation mode these apps are properly executed and finished by the production devices 16, i.e. an ongoing use case for this app is following a so-called happy path.

Parallel to the execution of this app, the focus machine 11 monitors via the first interface 14 the running use case of the app on at least one production device 16 (step S1).

If an error state of the monitored running use case is detected by the focus machine 11, it takes over the responsibility of the running use case (step S2). For example, an error state denotes the case that the detected state of a running use case fulfills at least one predefined condition, such as a dead end situation where the app is stopped.

Then, the focus machine 11 analyzes in step S3 the detected error state of the running use case. For this purpose, the focus machine 11 compares via the second interface the state of the running use case and the corresponding error state with data derived from the action plan repository 12.

Based on the analyzed error state of the running use case, the focus machine 11 fetches at least one suitable action out of a plurality of actions deposited in the action plan repository 12 (step S4).

Then, the running use case or parts of it are completed or at least terminated by the focus machine 11 (step S5). This is done by employing the obtained actions on the app.

Finally, the data of the completed use case or parts of it are provided to the production device 16 and/or the runtime environment (step S6).

Figure 3B:
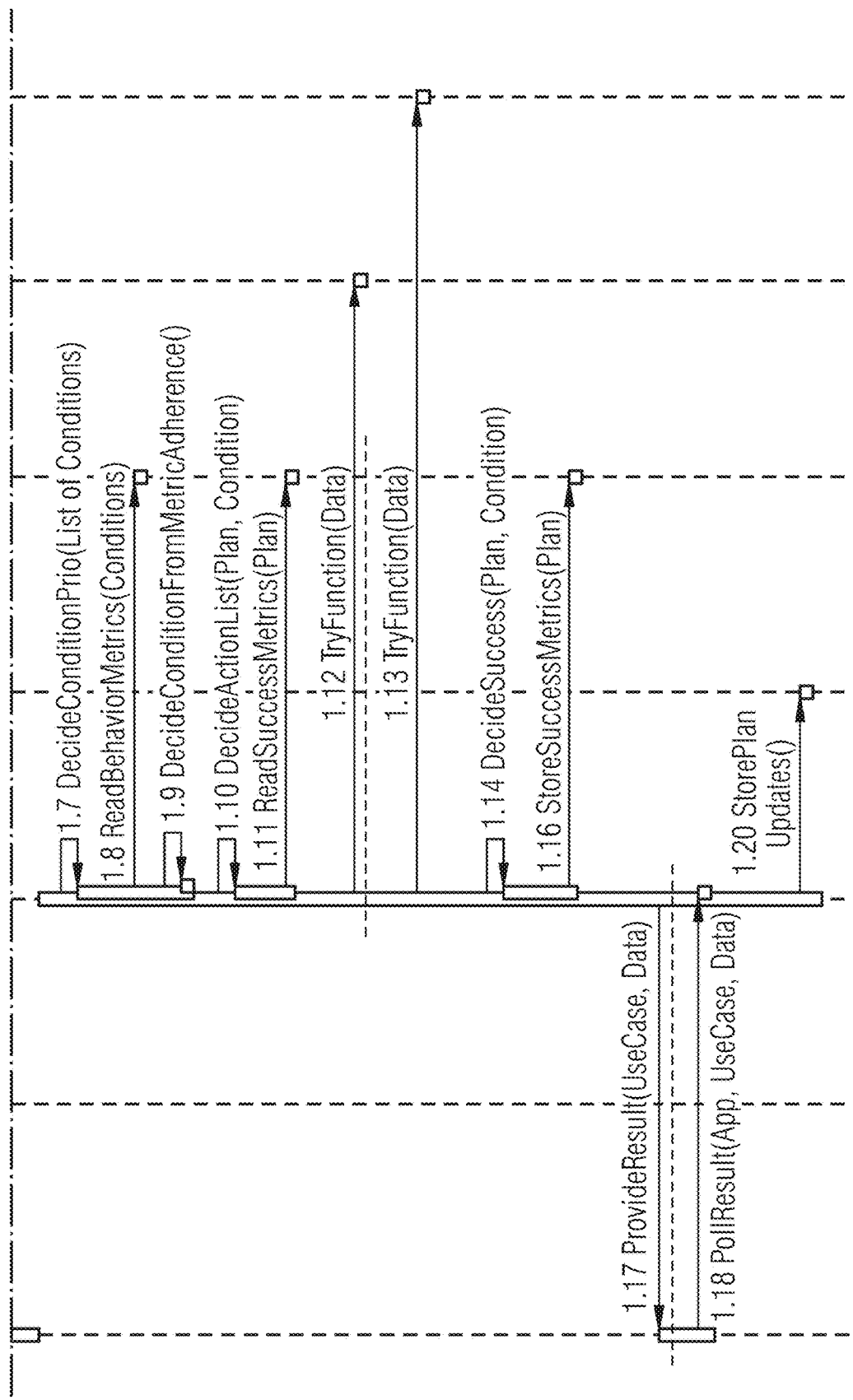
FIG. 3 is a representative view of FIGS. 3A and 3B and FIGS. 3A and 3B show a sequence diagram illustrating a further embodiment of the present invention.

FIG. 3 shows a sequence diagram illustrating a further embodiment of the invention in order to illustrate the scope of possible functions of an embodiment of the present invention.

On the left side of FIG. 3, the components of the production devices 16 are shown. These include at least one device 20 which is configured to execute one or more apps and a corresponding log repository 21.

The components on the right side include the components of the runtime system 10, in particular the focus machine 11, the plan repository 12, the behavior repository 23 and at least one action unit 24. The plan repository 22, behavior repository 23 and action unit 24 are typically part of the action plan repository 12.

When the device 20 of a healthcare runtime environment is executing an app, in particular an app having a medical content, or within a medical environment, the corresponding log data are provided to the log repository 21 (step 1.1).

The corresponding status of the running use case is communicated to the focus machine 11 (step 1.2). Alternatively, the status of a running use case may also be gathered by the focus machine 11 from the log repository 21 directly. This allows the focus machine 11 to detect the running use cases.

The focus machine 11 takes over the responsibility of the running use case if a predefined condition is met, e.g. an error state (step 1.4). The focus machine stores corresponding log data into the log repository 21 (step 1.3).

The focus machine 11 then generates a priority of conditions from a list of available conditions (step 1.7). The focus machine 11 has gathered this list of available conditions in an earlier stage, e.g. initially when the focus machine 11 has read the content of the action plan repository 22 (step 1.0). In particular, the focus machine 11 evaluates which conditions are principally available and what is a typical or standard reaction in the present stage and for the given scenario.

After having generated the priority of conditions, the focus machine 11 reads from the behavior repository 23 suitable behavior metrics which correspond to the generated conditions (step 1.8). With this information, the focus machine 11 is able to decide which condition is to be applied in the present stage of the use case and for the given scenario (step 1.9). On the basis of this information, the actions and the order in which they are executed in the present stage of the use case are determined (step 1.10).

Additionally, but not compulsory, the focus machine 11 may also derive other background information from the behavior repository 23, such as success metrics (step 1.11).

Hereinafter, the focus machine 11 tries to complete or at least terminate the running use case or use case stage by employing an action or a sequence of actions that have been derived from the action plan (steps 1.12, 1.13). For this purpose, the focus machine 11 provides functions and data for the faulty use case which affects the protection device 16.

Optionally, but not compulsory, the focus machine 11 then monitors and checks the condition and success of the actions taken (step 1.14). The corresponding data are stored in the behavior repository 23 (step 1.16).

Finally, the focus machine 11 provides the result of the faulty use case that was completed or terminated in the way described above, to the executable app of the device 20. This may be done by means of a push-process from the focus machine 11 to the device 20 (step 1.17) or a pull-process from the device 20 to the focus machine 11 (step 1.18).

Optionally, but not compulsory, the action plan used by the focus machine 11 for completing or terminating a faulty use case may be stored in the action plan repository 22. This enables the focus machine 11 to download an updated list of available action plans for a possible error state of a subsequentially executed app (step 1.0).

In the foregoing specification, the invention has been described with reference to specific examples of embodiments of the invention. It will, however, be evident that various modifications and changes may be made therein without departing from the broader spirit and scope of the invention as set forth in the appended claims.

Because the apparatuses are implementing the present invention are, for the most part, composed of electronic components known to those skilled in the art, details of these components will not be explained in any greater extent than that considered necessary as illustrated above, for the understanding and appreciation of the underlying concepts of the present invention and in order not to obfuscate or distract from the teachings of the present invention.

Furthermore, the devices may also be physically distributed over a number of apparatuses, while functionally operating as a single device. Devices functionally forming separate devices may be integrated in a single physical device. Those skilled in the art will recognize that the boundaries between logic and functional blocks are merely illustrative and that alternative embodiments may merge logic or functional blocks or impose an alternate decomposition of functionality upon various logic or functional blocks.

In the description, any reference signs shall not be construed as limiting the claim. The word "comprising" does not exclude the presence of other elements or steps then those listed in a claim. Furthermore, the terms "a" or "an", as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same applies for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage. The order of steps as presented in a claim does not prejudice the order in which the steps may actually be carried out, unless specifically recited in the claim.

Skilled artisans will appreciate that the illustrations of chosen elements in the drawings are only used to help to improve the understanding of the functionality and the arrangements of these elements in various embodiments of the present invention. Also, common and well understood elements that are useful or necessary in a commercially feasible embodiment are generally not depicted in the drawings in order to facilitate the understanding of the technical concept of these various embodiments of the present invention. It will further be appreciated that certain procedural stages in the described methods may be described or depicted in a particular order of occurrence while those skilled in the art will understand that such specificity with respect to sequence is not actually required.

In the context of software or information modeling, a happy path denotes a default scenario featuring no exceptional or error conditions, such as a best path.

In software engineering, a use case is a list of actions or event steps typically defining the interactions between a role (in UML known as an actor) and a system in order to achieve an objective.

An action plan repository denotes a suitable data or object storage device. The data storage device may be a computer memory device, such as a database, register, memorydisc or drive, DRAM, etc. An object storage device (also known as object-based storage) is a computer data storage architecture that manages data as objects, as opposed to other storage architectures like file systems which manages data as a file hierarchy, and block storage which manages data as blocks within sectors and tracks. Object storages are often used in a cloud-based architecture.

A focus machine is typically part of a program-controlled equipment, such as a computer, micro-processor, microcomputer, DSP, CPU, and the like.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented runtime system operable to provide a continuous product execution runtime environment for at least one application via a network, the network including a plurality of production devices configured to process information of the runtime environment, the computer-implemented runtime system comprising:
an action plan repository configured to store a plurality of actions; and
a focus machine, including a microprocessor, communicatively coupled to the action plan repository and the plurality of production devices, the focus machine configured to provide an autonomous runtime environment by at least:
monitoring a running use case of at least one application on at least one device via the focus machine;
taking over responsibility of the monitored running use case of the at least one application externally via the focus machine, upon an error state being detected for the monitored running use case;
analyzing the error state of the monitored running use case, externally via the focus machine;
obtaining at least one suitable substitution action out of the plurality of actions stored in the action plan repository, based on the error state of the monitored running use case analyzed; and
terminating and completing at least a part of the monitored running use case via the focus machine, by employing the at least one suitable substitution action obtained, on the at least one application.

2. The computer-implemented runtime system of claim 1, wherein the focus machine is further configured to provide data of the at least a part of the monitored running use case completed to at least one of the production devices and the runtime environment.

3. The computer-implemented runtime system of claim 2, wherein providing the data of the completed at least a part of the running use case includes:
storing via the focus machine, the data of the completed at least a part of the running use case, in the action plan repository.

4. The computer-implemented runtime system of claim 1, wherein the taking over of the responsibility includes:
detecting the error state of the monitored running use case, via the focus machine, upon a state of the monitored running use case fulfilling at least one condition.

5. The computer-implemented runtime system of claim 4, wherein the at least one condition includes a dead-end situation where execution of a corresponding application is stopped.

6. The computer-implemented runtime system of claim 4, wherein the at least one condition includes a deviation of the application executed from a happy path of the use case.

7. The computer-implemented runtime system of claim 1, wherein the taking over of the responsibility and the analyzing of the detected error state include:
generating, via the focus machine, a priority of conditions from a list of available conditions; and
reading from the action plan repository, via the focus machine, suitable behavior metrics corresponding to the priority of conditions generated.

8. The computer-implemented runtime system of claim 7, wherein the obtaining of the at least one suitable substitution action includes:
deciding, via the focus machine, which condition is to be applied in a present stage of the use case; and
determining, via the focus machine, the actions and an order in which the actions are to be executed, in the present stage of the use case.

9. The computer-implemented runtime system of claim 1, wherein the terminating of at least a part of the monitored running use case includes an autonomous success control monitoring by the focus machine by monitoring success of the employed at least one suitable substitution action and by storing success information in the action plan repository.

10. The computer-implemented runtime system of claim 1, wherein:
the network includes the plurality of production devices operable by a plurality of users and configured to process the information; and
the computer-implemented runtime system includes at least one second interface for coupling to the plurality of production devices and configured to provide the autonomous runtime environment for the plurality of production devices.

11. The computer-implemented runtime system of claim 10, wherein the network is configured to provide a cloud-based runtime environment.

12. The computer-implemented runtime system of claim 2, wherein providing the data of the completed at least a part of the running use case includes:
storing via the focus machine, the data of the completed at least a part of the running use, in the action plan repository.

13. The computer-implemented runtime system of claim 2, wherein the taking over of the responsibility includes:
  detecting the error state of the monitored running use case, via the focus machine, upon a state of the monitored running use case fulfilling at least one condition.

14. The computer-implemented runtime system of claim 13, wherein the at least one condition includes a dead-end situation execution of the corresponding application is stopped.

15. The computer-implemented runtime system of claim 5, wherein the at least one condition includes a deviation of the executed application from a happy path of the running use case.

16. The computer-implemented runtime system of claim 2, wherein the taking over of the responsibility and the analyzing of the detected error state include:
  generating, via the focus machine, a priority of conditions from a list of available conditions; and
  reading from the action plan repository, via the focus machine, suitable behavior metrics corresponding to the priority of conditions generated.

17. The computer-implemented runtime system of claim 16, wherein the obtaining of the at least one suitable substitution action includes:
  deciding, via the focus machine, which condition is to be applied in a present stage of the use case; and
  determining, via the focus machine, the actions and an order in which the actions are to be executed, in the present stage of the use case.

18. The computer-implemented runtime system of claim 1, further comprising:
  at least one first interface configured to communicatively couple the plurality of production devices to the focus machine; and
  at least one second interface configured to communicatively couple the focus machine to the action plan repository.

19. A computer-implemented runtime method of providing a continuous and autonomous product execution runtime environment for at least one application, comprising:
  providing a network including a plurality of production devices, configured to process information of the runtime environment;
  monitoring a running use case of an application on at least one production device, of the plurality of production devices, via an interface of the network;
  taking over responsibility of the running use case of the at least one application via an externally provided focus machine, upon an error state being detected for the running use case monitored;
  analyzing the error state of the running use case detected, via the focus machine;
  obtaining at least one suitable action out of a plurality of actions, based on the error state of the running use case analyzed; and
  terminating and completing at least a part of the running use case via the focus machine, by employing the at least one obtained suitable action on the at least one application.

20. The computer-implemented runtime method of claim 19, further comprising a non-transitory computer program product storing a set of instructions configured to be executed by a computerized device.

21. The computer-implemented runtime method of claim 19, further comprising a non-transitory computer readable medium storing a set of instructions configured to be executed by a computerized device.

* * * * *